US011103586B2

(12) United States Patent
Wood et al.

(10) Patent No.: US 11,103,586 B2
(45) Date of Patent: Aug. 31, 2021

(54) EXOSOMES FOR DELIVERY OF BIOTHERAPEUTICS (71) Applicant: Oxford University Innovation Limited, Oxford (GB)

(72) Inventors: Matthew Wood, Oxford (GB); Samira Lakhal-Littleton, Oxford (GB); Samir El Andaloussi, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 792 days.

(21) Appl. No.: 14/363,685

(22) PCT Filed: Dec. 7, 2012

(86) PCT No.: PCT/GB2012/053052
§ 371 (c)(1),
(2) Date: Jun. 6, 2014

(87) PCT Pub. No.: WO2013/084000
PCT Pub. Date: Jun. 13, 2013

(65) Prior Publication Data
US 2014/0356382 A1    Dec. 4, 2014

(30) Foreign Application Priority Data
Dec. 7, 2011 (GB) ..................... 1121070

(51) Int. Cl.
*A61K 39/44* (2006.01)
*A61K 47/42* (2017.01)
*A61K 35/36* (2015.01)
*A61K 9/127* (2006.01)
*A61K 47/58* (2017.01)
*A61K 47/62* (2017.01)
*A61K 47/68* (2017.01)
*A61K 39/00* (2006.01)
*A61K 47/69* (2017.01)
*A61K 38/00* (2006.01)

(52) U.S. Cl.
CPC ............ *A61K 47/42* (2013.01); *A61K 9/1271* (2013.01); *A61K 35/36* (2013.01); *A61K 39/00* (2013.01); *A61K 39/44* (2013.01); *A61K 47/58* (2017.08); *A61K 47/62* (2017.08); *A61K 47/6835* (2017.08); *A61K 47/6901* (2017.08); *A61K 38/00* (2013.01)

(58) Field of Classification Search
None
See application file for complete search history.

(56) References Cited

U.S. PATENT DOCUMENTS

| | | | |
|---|---|---|---|
| 6,627,421 B1 * | 9/2003 | Unger | C12M 35/02 204/157.62 |
| 6,685,911 B1 | 2/2004 | Zitvogel et al. | |
| 8,932,855 B2 * | 1/2015 | Gabrielsson | A61K 39/00 435/372.2 |
| 9,566,314 B2 * | 2/2017 | Thoene | A61P 25/00 |
| 10,233,445 B2 | 3/2019 | Seow et al. | |
| 10,329,561 B2 | 6/2019 | Seow et al. | |
| 10,704,047 B2 | 7/2020 | Seow et al. | |
| 2002/0090374 A1 | 7/2002 | Yarkoni et al. | |
| 2004/0024116 A1 | 2/2004 | Honnick | |
| 2004/0028647 A1 | 2/2004 | Zagury et al. | |
| 2004/0028692 A1 | 2/2004 | Zitvogel et al. | |
| 2004/0197314 A1 | 10/2004 | Delcayre et al. | |
| 2005/0153304 A1 * | 7/2005 | Gardner | C12Q 1/6897 435/6.16 |
| 2006/0222654 A1 | 10/2006 | Delcayre et al. | |
| 2007/0298118 A1 | 12/2007 | Lotvall et al. | |
| 2011/0177054 A1 | 7/2011 | Gibbings et al. | |
| 2013/0053426 A1 | 2/2013 | Seow et al. | |
| 2016/0067355 A1 | 3/2016 | Seow et al. | |
| 2017/0182182 A1 | 6/2017 | Seow et al. | |
| 2019/0153445 A1 | 5/2019 | Seow et al. | |
| 2020/0308587 A1 | 10/2020 | Seow et al. | |

FOREIGN PATENT DOCUMENTS

| | | |
|---|---|---|
| AU | 2004 203482 A1 | 8/2004 |
| CN | 1325441 A | 12/2001 |
| EP | 1537858 AL | 8/2005 |
| JP | 2006518219 | 8/2006 |
| WO | WO 1993/016552 A1 | 8/1993 |
| WO | WO 1997/05900 A1 | 2/1997 |
| WO | WO 2000/28001 A1 | 5/2000 |
| WO | WO 2001/36601 A1 | 5/2001 |
| WO | WO 2001/82958 A2 | 11/2001 |
| WO | WO 2003/016522 A2 | 2/2003 |
| WO | WO 2004/014954 A1 | 2/2004 |

(Continued)

OTHER PUBLICATIONS

Cho, I.S., et al., "Improved Serum Stability and Biophysical Properties of siRNAs Following Chemical Modifications", *Biotechnol. Lett.*, 30: 1901-1908 (2008).

Final Office Action for U.S. Appl No. 14/487,853, "Composition for Delivery of Genetic Material", dated Nov. 22, 2016.

Multiporator Basic Applications Manual, Eppendorf, pp. 27-50 (2006).

Notification of Transmittal of the International Search Report and Written Opinion of the International Searching Authority from counterpart Application No. PCT/GB2010/000762, "Composition for Delivery of Genetic Material", dated Aug. 2, 2010.

International Preliminary Examination Report on Patentability for PCT/GB2010/000762, dated Oct. 18, 2011 for Composition for Delivery of Genetic Material (4 pages).

(Continued)

*Primary Examiner* — Michail A Belyavskyi (74) *Attorney, Agent, or Firm* — Hamilton, Brook, Smith & Reynolds, P.C.

(57) ABSTRACT

The present invention relates to exosomes, loaded with biotherapeutic protein and/or peptide and methods of producing them and to the use of such exosomes for delivering protein and/or peptide in vivo, in particular the use of such exosomes in methods of therapy.

8 Claims, 2 Drawing Sheets

Specification includes a Sequence Listing.

(56) References Cited

FOREIGN PATENT DOCUMENTS

| WO | WO 2007/126386 A1 | 11/2007 |
|---|---|---|
| WO | WO 2008092153 * | 7/2008 |
| WO | WO 2010/119256 A1 | 10/2010 |
| WO | WO 2010/141716 A2 | 12/2010 |
| WO | WO 2011/000511 A2 | 1/2011 |

OTHER PUBLICATIONS

Temchura, V.V., et al., "Enhancement of Immunostimulatory Properties of Exosomal Vaccines by Incorporation of Fusion-Competent G Protein of Vesicular Stomatitis Virus", Vaccine, 26: 3662-3672 (2008).

United Kingdom Search Report for GB 0906693.7: "Composition and Method" dated Aug. 13, 2009 (2 pages).

United Kingdom Search Report for GB 0906692.9: "Composition" dated Aug. 13, 2009 (2 pages).

Zeng, et al., "A Synthetic Peptide Containing Loop 4 of Nerve Growth Factor for Targeted Gene Delivery", The Journal of Gene Medicine, 6: 1247-1256 (2004).

Altschul, S. F., "A Protein Alignment Scoring System Sensitive at All Evolutionary Distances", J Mol Evol, 36:290-300 (1993).

Altschul, S. F., et al., "Basic Local Alignment Search Tool", J Mol. Biol., 215:403-410 (1990).

Alvarez-Erviti, L., et al., "Delivery of siRNA to the Mouse Brain by Systemic Injection of Targeted Exosomes", Nature Biotechnology, 29(4):341-347 (2011).

Bio-Medicine, "Pharma Research Challenge", 2 pages downloaded on May 23, 2013 from URL:http://news.bio-medicine.org/?q=biology-technology/optimizing-electroporation-para . . . .

Chen, S.Q., et al., "[Production of Specific CTL Induced by Exosomes Derived from K562 Cells.]", Zhongguo Shi Yan Xue Ye Xue Za Zhi, 14(6):1168-1171 (2006) with English Abstract.

Delcayre, A. and Le Pecq, J.-B., "Exosomes as Novel Therapeutic Nanodevices", Current Opinion in Molecular Therapeutics, 8(1):31-38 (2006).

Delcayre, A., et al., "Exosome Display Technology: Applications to the Development of New Diagnostics and Therapeutics", Blood Cells, Molecules and Diseases, 35:158-168 (2005).

Devereaux, J., et al., "A Comprehensive Set of Sequence Analysis Programs for the VAX", Nucleic Acids Research, 12(1): 387-395 (1984).

Gallagher, J., Breakthrough in Delivering Drugs to the Brain, BBC News, 2 pages, downloaded on May 8, 2012 from URL: http://www.bbc.co.uk/news/health-12776222.

Grosse, S., et al.,"Potocytosis and Cellular Exit of Complexes as Cellular Pathways for Gene Delivery by Polycations", The Journal of Gene Medicine, 7:1275-1286 (2005).

Hao, S., et al., "Cancer Immunotherapy by Exosome-Based Vaccines", Cancer Biotherapy & Radiopharmaceuticals, 22(5):692-703 (2007).

Henikoff, S. and Henikoff, J.G., "Amino Acid Substitution Matrices from Protein Blocks", Proc. Natl. Acad. Sci., 89:10915-10919 (1992).

Karlin, S. and Altschul, S.F., "Applications and Statistics for Multiple High-Scoring Segments in Molecular Sequences", Proc. Natl. Acad. Sci.,90:5873-5877 (1993).

Luo, Z., et al., "Immunotherapy of Exosomes from DC Transfected with mRNA of Gastric Cancer Cells in Carried-Tumor Mice.", CAPULUS DN142:296329, 1 page (2003).

Luo, Z., et al., "Immunotherapy of Dendritic Cells and Its Exosomes Transfected with mRNA of Gastric Cancer Cells in Tumor-Carried Mice.", CAPULUS DN 143:24680, 1 page (2004).

Mendonça, L.S., et al., "Transferrin Receptor-Targeted Liposomes Encapsulating Anti-BCR-ABL siRNA or asODN for Chronic Myeloid Leukemia Treatment", Bioconjugate Chem., 21:157-168 (2010).

Morgan, W.F. and Day, J.P., "The Introduction of Proteins into Mammalian Cells by Electroporation" In Methods in Molecular Biology, J.A. Nickoloff ed. (NJ:Humana Press, Inc), pp. 63-71 (1995).

Qazi, K.R., et al., "Antigen-Loaded Exosomes Alone Induce Thl-Type Memory Through a B Cell-Dependent Mechanism", Blood, 113(12):2673-2683 (2009).

Quah, B.J.C. and O'Neill, H.C., "The Immunogenicity of Dendritic Cell-Derived Exosomes", Blood Cells, Molecules and Diseases, 35:94-110 (2005).

Raposo, G., et al., "B Lymphocytes Secrete Antigen-Presenting Vesicles", J. Exp. Med., 183:1161-1172 (1996).

Simhardri, V.R, et al., "Dendritic Cells Release HLA-B-Associated Transcript-3 Positive Exosomes to Regulate Natural Killer Function", PLoS ONE, 3(10):e3377, 8 pages (2008).

Skog, J., et al., "Glioblastoma Microvesicles Transport RNA and Proteing that Promote Tumour Growth and Provide Diagnostic Biomarkers", Nature Cell Biology, 10(12):1470-1476 (2008).

University of Oxford, Media web-page article, "New Method Delivers Alzheimers Drug to the Brain", updated Mar. 21, 2011, 4 pages, no author given, downloaded from URL: www.ox.ac.uk/media/new_stories/2011/112103.html.

Valadi, H., et al., "Exosome-Mediated Transfer of mRNAs and microRNAs is a Novel Mechanism of Genetic Exchange Between Cells", Nature Cell Biology, 9(6):654-659 (2007).

Zitvogel, L., et al., "Eradication of Established Murine Tumors Using a Novel Cell-Free Vaccine: Dendritic Cell-Derived Exosomes", Nature Medicine, 4(5):594-600 (1998).

Notification of Transmittal of the International Search Report and the Written Opinion of the International Search Authority for PCT/GB2012/053052, "Exosomes for Delivery of Biotherapeutics" dated Aug. 6, 2013.

International Preliminary Report on Patentability for PCT/GB2012/053052, "Exosomes for Delivery of Biotherapeutics" date of issuance Jun. 10, 2014.

Non-Final Office Action for U.S. Appl. No. 15/364,794, "Composition for Delivery of Genetic Material", dated Aug. 25, 2017.

Bader AG, et al "Developing therapeutic microRNAs for cancer" Gene Ther. 2011 18(12):1121-1126; published Jun. 2, 2011.

Chakrabarty et al "Transfer of monoclonal antibodies into mammalian cells by electroporation" J Biol Chem. 1989; 264 (26):15494-500; published Sep. 15, 1989.

Editorial (Ponsaerts and Berneman), "Modulation of cellular behavior by exogenous messenger RNA," Leukaemia, 20, 767-769; published May 1, 2006.

Holliger P & Hudson PJ "Engineered antibody fragments and the rise of single domains" Nat Biotechnol. 2005 ;23(9):1126-36; published Sep. 7, 2005.

Logozzi ,et al "High Levels of Exosomes Expressing CD63 and Caveolin-1 in Plasma of Melanoma Patients" PLoS ONE, vol. 4, No. 4, e5219, 10 pages, published Apr. 2009.

Ratacjzak et al., "Embryonic stem cell-derived microvesicles reprogram hematopoietic progenitors: evidence for horizontal transfer of mRNA and protein delivery," Leukaemia, 20, 847-856; published Feb. 2, 2006.

Notice of Allowance for U.S. Appl. No. 15/364,794, "Composition for Delivery of Genetic Material", dated Apr. 9, 2019.

Non-Final Office Action for U.S. Appl. No. 16/264,257, "Composition for Delivery of Genetic Material", dated Oct. 16, 2019.

Bot, A.I., et al., "Novel Lipid-Based Hollow-Porous Microparticles as a Platform for Immunoglobulin Delivery to the Respiratory Tract", Pharmaceutical Research, 17(3): 275-283 (2000).

Herceptin (trastuzumab) Prescribing Information, Oct. 2010, 33 pages.

Keizer, R.J., et al., "Clinical Pharmacokinetics of Therapeutic Monoclonal Antibodies", Clin Pharmacokinet 2010: 49(8): 493-507.

McLellan, A.D., "Exosome Release by Primary B Cells", Critical Reviews in Immunology, 29(3): 203-217 (2009).

Notice of Allowance for U.S. Appl. No. 16/264,257, "Composition for Delivery of Genetic Material", dated Apr. 3, 2020.

(56) References Cited

OTHER PUBLICATIONS

Förster, R., et al., "CCR7 and its ligands: balancing immunity and tolerance" Nature Reviews Immunology, vol. 8, Apr. 1, 2008, 362-371.
Hung, M. et al. "Stabilization of Exosome-targeting Peptides via Engineered Glycosylation" Journal of Biological Chemistry, 290(13), Feb. 5, 2015, 8166-8172.
Ko, Y.T., et al "Gene delivery into ischemic myocardium by double-targeted lipoplexes with antimyosin antibody and TAT peptide" Gene Therapy, vol. 16, pp. 52-59 (2009).
Kooijmans, S., et al., "Electroporation-induced siRNA precipitation obscures the efficiency of siRNA loading into extracellular vesicles" Journal of Controlled Release, vol. 172, Aug. 29, 2013, 229-238.
Seow, Y., et al., "Targeted Delivery of Plasmid DNA and siRNA with Modified Dendritic Cell-Derived Exosomes" Molecular Therapy, vol. 17, Supplement 1, May 2009.
Non-Final Office Action for U.S. Appl. No. 16/857,803, "Composition for Delivery of Genetic Material", dated Oct. 27, 2020.
Final Office Action for U.S. Appl. No. 16/857,803, "Composition for Delivery of Genetic Material", dated Feb. 3, 2021.
Wang, J., et al., "Host derived exosomes-pathogens interactions: Potential functions of exosomes in pathogen infection", Biomedicine & Pharmacotherapy, 108 (2018) 1451-1459.

\* cited by examiner

SEQUENCE LISTING

```
<160> NUMBER OF SEQ ID NOS: 3

<210> SEQ ID NO 1
<211> LENGTH: 415
<212> TYPE: PRT
<213> ORGANISM: Mus musculus

<400> SEQUENCE: 1

Met Cys Leu Ser Pro Val Lys Gly Ala Lys Leu Ile Leu Ile Phe Leu
1               5                   10                  15

Phe Leu Gly Ala Val Gln Ser Asn Ala Leu Ile Val Asn Leu Thr Asp
            20                  25                  30
```

```
Ser Lys Gly Thr Cys Leu Tyr Ala Glu Trp Glu Met Asn Phe Thr Ile
         35                  40                  45
Thr Tyr Glu Thr Thr Asn Gln Thr Asn Lys Thr Ile Thr Ile Ala Val
 50                  55                  60
Pro Asp Lys Ala Thr His Asp Gly Ser Cys Gly Asp Asp Arg Asn
 65                  70                  75                  80
Ser Ala Lys Ile Met Ile Gln Phe Gly Phe Ala Val Ser Trp Ala Val
                 85                  90                  95
Asn Phe Thr Lys Glu Ala Ser His Tyr Ser Ile His Asp Ile Val Leu
                100                 105                 110
Ser Tyr Asn Thr Ser Asp Ser Thr Val Phe Pro Gly Ala Val Ala Lys
                115                 120                 125
Gly Val His Thr Val Lys Asn Pro Glu Asn Phe Lys Val Pro Leu Asp
130                 135                 140
Val Ile Phe Lys Cys Asn Ser Val Leu Thr Tyr Asn Leu Thr Pro Val
145                 150                 155                 160
Val Gln Lys Tyr Trp Gly Ile His Leu Gln Ala Phe Val Gln Asn Gly
                165                 170                 175
Thr Val Ser Lys Asn Glu Gln Val Cys Glu Glu Asp Gln Thr Pro Thr
                180                 185                 190
Thr Val Ala Pro Ile Ile His Thr Thr Ala Pro Ser Thr Thr Thr Thr
                195                 200                 205
Leu Thr Pro Thr Ser Thr Pro Thr Pro Thr Pro Thr Pro Thr Pro Thr
                210                 215                 220
Val Gly Asn Tyr Ser Ile Arg Asn Gly Asn Thr Thr Cys Leu Leu Ala
225                 230                 235                 240
Thr Met Gly Leu Gln Leu Asn Ile Thr Glu Glu Lys Val Pro Phe Ile
                245                 250                 255
Phe Asn Ile Asn Pro Ala Thr Thr Asn Phe Thr Gly Ser Cys Gln Pro
                260                 265                 270
Gln Ser Ala Gln Leu Arg Leu Asn Asn Ser Gln Ile Lys Tyr Leu Asp
                275                 280                 285
Phe Ile Phe Ala Val Lys Asn Glu Lys Arg Phe Tyr Leu Lys Glu Val
                290                 295                 300
Asn Val Tyr Met Tyr Leu Ala Asn Gly Ser Ala Phe Asn Ile Ser Asn
305                 310                 315                 320
Lys Asn Leu Ser Phe Trp Asp Ala Pro Leu Gly Ser Ser Tyr Met Cys
                325                 330                 335
Asn Lys Glu Gln Val Leu Ser Val Ser Arg Ala Phe Gln Ile Asn Thr
                340                 345                 350
Phe Asn Leu Lys Val Gln Pro Phe Asn Val Thr Lys Gly Gln Tyr Ser
                355                 360                 365
Thr Ala Gln Glu Cys Ser Leu Asp Asp Thr Ile Leu Ile Pro Ile
                370                 375                 380
Ile Val Gly Ala Gly Leu Ser Gly Leu Ile Ile Val Ile Val Ile Ala
385                 390                 395                 400
Tyr Leu Ile Gly Arg Arg Lys Thr Tyr Ala Gly Tyr Gln Thr Leu
                405                 410                 415

<210> SEQ ID NO 2
<211> LENGTH: 27
<212> TYPE: PRT
<213> ORGANISM: Artificial Sequence
<220> FEATURE:
<223> OTHER INFORMATION: transportan
```

```
<400> SEQUENCE: 2

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 3
<211> LENGTH: 81
<212> TYPE: DNA
<213> ORGANISM: Artificial Sequence
<220> FEATURE:
<223> OTHER INFORMATION: transportan

<400> SEQUENCE: 3
ggctggaccc tgaacagcgc gggctatctg ctgggcaaaa ttaacctgaa agcgctggcg    60
gcgctggcga aaaaaattct g                                              81
```

EXOSOMES FOR DELIVERY OF BIOTHERAPEUTICS

This application is the U.S. National Stage of International Application No. PCT/GB2012/053052, filed Dec. 7, 2012, which designates the U.S., published in English, and claims priority under 35 U.S.C. §§ 119 or 365(c) to Great Britain Application No. 1121070.5, filed Dec. 7, 2011.

INCORPORATION BY REFERENCE OF MATERIAL IN ASCII TEXT FILE

This application incorporates by reference the Sequence Listing contained in the following ASCII text file:

a) File name: 47761005000SEQLISTFINAL.txt; created Jul. 24, 2014, 5 KB in size.

FIELD OF THE INVENTION

The present invention relates to compositions for the delivery of protein or peptide, including antibody and antibody fragments. In particular the present invention relates to exosomes, loaded with protein or peptide and methods of producing them.

BACKGROUND TO THE INVENTION

Biotherapeutic agents are routinely used in the treatment and/or prevention of a wide range of diseases, including cancer, genetic disorders and autoimmune diseases. Biotherapeutic agents are typically protein or peptides, for example antibodies or antibody fragments and tend to be administered in naked form, i.e. without any aid to delivery. However, in some instances, for example due to rapid clearance, lack of organ-specific distribution and low efficacy of cellular uptake, administering biotherapeutics in specialized delivery vehicles would be desirable.

Exosomes are small membrane-bound vesicles (30-100 nm) of endocytic origin that are released into the extracellular environment following fusion of multivesicular bodies with the plasma membrane. Exosome production has been described for many immune cells including B cells, T cells, and dendritic cells (DCs). Exosomes derived from B lymphocytes and mature DCs express MHC-II, MHC-I, CD86 and ICAM-1 [1, 2], and have been used to induce specific anti-tumor T cytotoxic responses and anti-tumor immunity in experimental models and clinical trials [2, 3]. The potential of exosome-mediated gene delivery has been shown with delivery of murine mRNAs and miRNAs to human mast cells [4] and glioma-derived exosomes [5] have been demonstrated to transfer mRNAs produced by exogenous DNA plasmids to heterologous cells. Exosomes with exogenous DNA, siRNAs and other modified oligonucleotides have also been disclosed [6].

SUMMARY OF THE INVENTION

The present inventors have successfully loaded exosomes with exogenous protein, and in particular exogenous antibodies. Thus the present invention relates to methods for loading exosomes with exogenous protein and/or peptide, including antibodies and fragments thereof, the exosomes loaded with such exogenous protein and/or peptides, and their use in delivery of the protein and/or peptides for therapy.

The exosomes of the present invention may have a targeting moiety expressed on their surface. Fusion proteins comprising exosomal transmembrane proteins and a targeting moiety allowing for the expression of the targeting moiety on the surface of the exosomes and nucleic acid constructs encoding such fusion proteins are also described. The exosomes comprising targeting moieties can be loaded with exogenous protein and/or peptides, including antibodies or fragments thereof, according to the invention and used in delivery of the protein and/or peptides for therapy.

In accordance with one aspect of the present invention, there is provided a composition comprising an exosome, wherein the exosome is loaded with exogenous protein and/or peptide.

In another aspect, the invention provides a composition comprising an exosome containing protein and/or peptide, wherein the exosome is derived from an immature dendritic cell, for use in a method of delivering the protein and/or peptide in vivo.

In another embodiment, the invention provides a method of loading exosomes with protein and/or peptide comprising providing a composition of exosomes, and loading the exosomes with protein and/or peptide by electroporation.

In another embodiment, the invention provides a method of loading exosomes with protein and/or peptide comprising providing a composition of exosomes and loading the exosomes with protein and/or peptide by transfection, using a cationic liposome transfection agent.

DETAILED DESCRIPTION OF THE INVENTION

The present invention is directed to exosomes, and their use as delivery vehicles for protein and/or peptide biotherapeutics, including antibodies and antibody fragments. Exosomes are small membrane-bound vesicles of endocytic origin that are released into the extracellular environment following fusion of multivesicular bodies with the plasma membrane. Thus, the present application is directed to a composition comprising such exosomes. Typically, the exosomes are between 30 and 100 nm in diameter but can include membrane particles of similar origin up to 200 nm. Exosomes as used herein refers to nanoparticles of endosomal origin that are secreted from multivesicular bodies.

Exosomes are produced by many different types of cells including immune cells such as B lymphocytes, T lymphocytes, dendritic cells (DCs) and mast cells. Exosomes are also produced, for example, by glioma cells, platelets, reticulocytes, neurons, intestinal epithelial cells, tumour cells, HELA cells, human embryonic kidney cells (HEK cells), B2M17 cells, Bend3 cells, primary bone marrow-derived dendritic cells, BV-2 microglia cells and NEURO2A cells. Exosomes for use in accordance with the present application can be derived from any suitable cell, including the cells identified above. Exosomes have also been isolated from physiological fluids, such as plasma, urine, amniotic fluid and malignant effusions.

In a preferred aspect of the present invention, exosomes are derived from DCs, preferably immature DCs. Exosomes produced from immature DCs do not express MHC-II, MHC-I or CD86. As such, such exosomes do not stimulate naïve T cells to a significant extent and are unable to induce a response in a mixed lymphocyte reaction. Thus exosomes produced from immature dendritic cells are ideal candidates for use in delivery of protein and/or peptide biotherapeutics, particularly for in vivo use, for example, in the treatment of cancer and autoimmune conditions.

Thus, in accordance with the first aspect of the present invention, exosomes derived from dendritic cells are provided for use in in vivo delivery of protein and/or peptide.

As outlined above, exosomes are produced by many different types of cell and have also been isolated from physiological fluids. Thus, in accordance with the present invention, exosomes can be obtained from any suitable cell type as discussed above, or by isolation from physiological fluids. Typically, the methods of the present invention comprise isolation of the exosomes from cell culture medium or tissue supernatant.

Exosomes produced from cells can be collected from the culture medium by any suitable method. Typically a preparation of exosomes can be prepared from cell culture or tissue supernatant by centrifugation, filtration or combinations of these methods. For example, exosomes can be prepared by differential centrifugation, that is low speed (<20000 g) centrifugation to pellet larger particles followed by high speed (>100000 g) centrifugation to pellet exosomes, size filtration with appropriate filters (for example, 0.22 μm filter), gradient ultracentrifugation (for example, with sucrose gradient) or a combination of these methods.

In accordance with the present invention, the exosomes are loaded with exogenous protein and/or peptide. In particular, in accordance with the present invention, exosomes are prepared and then loaded with the desired protein and/or peptide for delivery. In another aspect, the protein or peptide can be loaded in the exosomes by overexpression of the protein or peptide in the cell which is used to produce the exosomes, so that the exosomes can be loaded with the peptide or protein. Exogenous refers to a protein with which the exosome is not normally associated.

The use of exosomes to deliver biotherapeutics offers a number of advantages over conventional means of delivering such compounds. For example, when biotherapeutics are delivered using exosomes they are protected from degradation and are more stable; biotherapeutics may be delivered to a target tissue, such as a specific type of cancer, more efficiently and/or more specifically than if not encapsulated inside exosomes; and/or the cargo may be less likely to elicit an immune response because it is contained within exosomes and so is not freely available for detection by immune cells and/or binding to antibodies. Other potential advantages of the use of exosomes to deliver biotherapeutics include bypassing hepatic cells following systemic delivery of exosomes and/or avoiding drug resistance, such as the upregulation of drug transporters such as ABC-transporters.

Suitable protein and/or peptide for delivery include exogenous antibodies and antibody fragments. In accordance with one aspect of the present invention, the protein and/or peptide loaded into the exosome is not protein and/or peptide that is typically associated with the exosomes, for example, the protein and/or amino acid is preferably not an protein or a peptide which is incorporated into an exosome on its production from a cell. In particular, the present invention is concerned with the ability to load protein and/or peptide into an exosome preparation that has already been isolated from cells. Thus exogenous protein and/or peptide refers to protein and/or peptide inclusive of proteins and peptides that are not normally associated with exosomes. In particularly preferred embodiments, the protein and/or peptide is an antibody and/or antibody fragment which is not typically found in exosomes.

Any biotherapeutic protein and/or peptide that has utility in the treatment and/or prevention of a condition, disease or disorder may be incorporated into exosomes according to the present invention. In a preferred embodiment the protein or peptide for incorporation into the exosomes is an antibody or an antibody fragment.

The protein and/or peptide to be loaded into the exosomes is chosen on the basis of the desired effect of that protein and/or peptide on the cell into which it is intended to be delivered and the mechanism by which that effect is to be carried out. A single protein or peptide may be incorporated into the exosomes. Alternatively, more than one protein and/or peptide may be incorporated into the exosomes. The more than one proteins and/or peptides may act on the same or different targets to bring about their therapeutic and/or preventative effect.

In a preferred aspect of the present invention, the peptide or biotherapeutic protein for delivery is not one which is used to generate an immune response. In particular the protein is typically derived from a human protein, and is not a peptide entirely of non-human origin, when used to treat a human. Typically the peptide is not derived from a bacteria, virus or other infectious agent. Also the peptide or protein is not selected from or derived from a tumour antigen. Thus the peptide or protein is selected to provide a therapeutic benefit itself, and is not intended to be used to generate an immune response against the peptide or protein.

The proteins and/or peptides to be incorporated into the exosomes may be useful, for example, in the treatment and/or prevention of cancer. Examples of cancers that may be treated using protein or peptide biotherapeutics include leukaemia, colorectal cancer, head and neck cancer, non-Hodgkin lymphoma, breast cancer, ovarian cancer, prostate cancer, gastric cancer, pancreatic cancer, adenocarcinoma and solid tumours. Such biotherapeutic proteins and/or peptides are typically antibodies or fragments thereof, particularly monoclonal antibodies or fragments thereof.

Protein and/or peptide biotherapeutics may also be used in the treatment and/or prevention of autoimmune conditions. Autoimmune conditions arise from an overactive immune response of the body against substances, tissues and organs normally present in the body.

Biotherapeutic proteins and/or peptides loaded into exosomes according to the present invention may also be used to treat and/or prevent other conditions, including cardiovascular disease, haemophilia, sepsis, stroke, muscular dystrophy, including Duchenne muscular dystrophy (DMD), macular degeneration and Alzheimer's Disease.

In a preferred embodiment, the biotherapeutic loaded into exosomes according to the present invention is a therapeutic antibody. In a more preferred embodiment, the therapeutic antibody is selected from a monoclonal antibody for blocking the active site of Bace-1 and b-amyloids; a monoclonal antibody against gliblastoma kinases and an antibody against α4-integrin for the treatment of MS, for example Natalizumab.

In a preferred embodiment the biotherapeutic loaded into exosomes according to the present invention is a peptide. In a more preferred embodiment the peptide is selected from an immune-dominant peptide for eliciting immune responses to viral and/or tumour antigens; a neuroprotective peptide such as a δ-opioid receptor ligand, for example Biphalin; an immune-suppressive peptide for neuroinflammation, for example adrenomedullin and a NBD peptide that binds and inhibits NfKB signalling.

The exogenous protein and/or peptide can be introduced into the exosomes by a number of different techniques. In particularly preferred embodiments of the invention, the exosomes are loaded by electroporation or the use of a transfection reagent. The present inventors have identified that despite the small size of exosomes, it is still possible to use electroporation to load the exosomes with the exogenous protein and/or peptide. This is surprising in view of the small size of the exosomes compared to cells. Extrapolation of the voltages used for electroporation of cells to take into account the size of the exosomes would suggest that excessively high voltages would be required for electroporation of exosomes. Surprisingly however, the present inventors have identified that it is possible to use electroporation to load exosomes with antibodies. Electroporation conditions may vary depending on the charge and size of the biotherapeutic cargo. Typical voltages are in the range of 20V/cm to 1000V/cm, such as 20V/cm to 100V/cm with capacitance typically between 25 μF and 250 μF, such as between 25 μF and 125 μF. A voltage in the range of 150 mV to 250 mV, particularly a voltage of 200 mV is preferred for loading exosomes with an antibody according to the present invention.

Alternatively, the exosomes may be loaded with exogenous protein and/or peptide using a transfection reagent. Despite the small size of the exosomes, conventional transfection agents may be used for transfection of exosomes with protein and/or peptide. Preferred transfection reagents for use in accordance with the present invention include cationic liposomes.

In another embodiment, exosomes may also be loaded by transforming or transfecting a host cell with a nucleic acid construct which expresses therapeutic protein or peptide of interest, such that the therapeutic protein or peptide is taken up into the exosomes as the exosomes are produced from the cell.

Antibodies

As described herein, in a preferred embodiment, the protein and/or peptide to be incorporated into the exosomes is an antibody or antibody fragment. The term "antibody" as referred to herein includes whole antibodies and any antigen binding fragment (i.e., "antigen-binding portion") or single chains thereof. An antibody refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. Each light chain is comprised of a light chain variable region (abbreviated herein as $V_L$) and a light chain constant region. The variable regions of the heavy and light chains contain a binding domain that interacts with an antigen. The $V_H$ and $V_L$ regions can be further subdivided into regions of hypervariability, termed complementarity determining regions (CDR), interspersed with regions that are more conserved, termed framework regions (FR).

The constant regions of the antibodies may mediate the binding of the immunoglobulin to host tissues or factors, including various cells of the immune system (e.g., effector cells) and the first component (Clq) of the classical complement system.

An antibody of use in the invention may be a monoclonal antibody or a polyclonal antibody, and will preferably be a monoclonal antibody. An antibody of use in the invention may be a chimeric antibody, a CDR-grafted antibody, a nanobody, a human or humanised antibody or an antigen binding portion of any thereof. For the production of both monoclonal and polyclonal antibodies, the experimental animal is typically a non-human mammal such as a goat, rabbit, rat or mouse but may also be raised in other species such as camelids.

Polyclonal antibodies may be produced by routine methods such as immunisation of a suitable animal, with the antigen of interest. Blood may be subsequently removed from the animal and the IgG fraction purified.

Monoclonal antibodies (mAbs) of use in the invention can be produced by a variety of techniques, including conventional monoclonal antibody methodology e.g., the standard somatic cell hybridization technique of Kohler and Milstein. The preferred animal system for preparing hybridomas is the murine system. Hybridoma production in the mouse is a very well-established procedure and can be achieved using techniques well known in the art.

The term "antigen-binding portion" of an antibody refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include a Fab fragment, a F(ab')$_2$ fragment, a Fab' fragment, a Fd fragment, a Fv fragment, a dAb fragment and an isolated complementarity determining region (CDR). Single chain antibodies such as scFv antibodies are also intended to be encompassed within the term "antigen-binding portion" of an antibody. These antibody fragments may be obtained using conventional techniques known to those of skill in the art, and the fragments may be screened for utility in the same manner as intact antibodies.

An antibody of use in the invention may be prepared, expressed, created or isolated by recombinant means, such as (a) antibodies isolated from an animal (e.g., a mouse) that is transgenic or transchromosomal for the immunoglobulin genes of interest or a hybridoma prepared therefrom, (b) antibodies isolated from a host cell transformed to express the antibody of interest, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

An antibody of use in the invention may be a human antibody or a humanised antibody. The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of use in the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

Such a human antibody may be a human monoclonal antibody. Such a human monoclonal antibody may be produced by a hybridoma which includes a B cell obtained from a transgenic nonhuman animal, e.g., a transgenic mouse, having a genome comprising a human heavy chain transgene and a light chain transgene fused to an immortalized cell.

Human antibodies may be prepared by in vitro immunisation of human lymphocytes followed by transformation of the lymphocytes with Epstein-Barr virus.

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

Targeting

The exosomes of the present invention may be targeted to a desired cell type or tissue. This targeting is achieved by expressing on the surface of the exosome a targeting moiety which binds to a cell surface moiety expressed on the surface of the cell to be targeted. Typically the targeting moiety is a peptide which is expressed as a fusion protein with a transmembrane protein typically expressed on the surface of the exosome.

In more detail, the exosomes of the invention can be targeted to particular cell types or tissues by expressing on their surface a targeting moiety such as a peptide. Suitable peptides are those which bind to cell surface moieties such as receptors or their ligands found on the cell surface of the cell to be targeted. Examples of suitable targeting moieties are short peptides, scFv and complete proteins, so long as the targeting moiety can be expressed on the surface of the exosome and does not interfere with insertion of the membrane protein into the exosome. Typically the targeting peptide is heterologous to the transmembrane exosomal protein. Peptide targeting moieties may typically be less than 100 amino acids in length, for example less than 50 amino acids in length, less than 30 amino acids in length, to a minimum length of 10, 5 or 3 amino acids.

Targeting moieties can be selected to target particular tissue types such as muscle, brain, liver, pancreas and lung for example, or to target a diseased tissue such as a tumour. In a particularly preferred embodiment of the present invention, the exosomes are targeted to brain tissue.

Specific examples of targeting moieties include muscle specific peptide, discovered by phage display, to target skeletal muscle, a 29 amino acid fragment of Rabies virus glycoprotein that binds to the acetylcholine receptor or a fragment of neural growth factor that targets its receptor to target neurons, the peptide transportan, and secretin peptide that binds to the secretin receptor can be used to target biliary and pancreatic epithelia. As an alternative, immunoglobulins and their derivatives, including scFv antibody fragments can also be expressed as a fusion protein to target specific antigens, such as VEGFR for cancer gene therapy. As an alternative, natural ligands for receptors can be expressed as fusion proteins to confer specificity, such as NGF which binds NGFR and confers neuron-specific targeting.

The peptide targeting moiety is expressed on the surface of the exosome by expressing it as a fusion protein with an exosomal transmembrane protein. A number of proteins are known to be associated with exosomes; that is they are incorporated into the exosome as it is formed. The preferred proteins for use in targeting the exosomes of the present invention are those which are transmembrane proteins. Examples include but are not limited to Lamp-1, Lamp-2, CD13, CD86, Flotillin, Syntaxin-3, CD2, CD36, CD40, CD40L, CD41a, CD44, CD45, ICAM-1, Integrin alpha4, LiCAM, LFA-1, Mac-1 alpha and beta, Vti-1A and B, CD3 epsilon and zeta, CD9, CD18, CD37, CD53, CD63, CD81, CD82, CXCR4, FcR, GluR2/3, HLA-DM (MHC II), immunoglobulins, MHC-I or MHC-II components, TCR beta and tetraspanins. In particularly preferred embodiments of the present invention, the exosomes loaded with biotherapeutic protein and/or peptide are targeted using a transmembrane protein selected from Lamp-1, Lamp-2, CD13, CD86, Flotillin, Syntaxin-3. In a particularly preferred embodiment the transmembrane protein is Lamp-2. The sequence of Lamp-2 is set out in SEQ ID NO: 1.

The following section relates to general features of all polypeptides, and in particular to variations, alterations, modifications or derivatisations of amino acid sequence. It will be understood that such variations, alterations, modifications or derivatisations of polypeptides as are described herein are subject to the requirement that the polypeptides retain any further required activity or characteristic as may be specified subsequent sections of this disclosure.

Variants of polypeptides may be defined by particular levels of amino acid identity which are described in more detail in subsequent sections of this disclosure. Amino acid identity may be calculated using any suitable algorithm. For example the PILEUP and BLAST algorithms can be used to calculate homology or line up sequences (such as identifying equivalent or corresponding sequences (typically on their default settings), for example as described in Altschul S. F. (1993) J Mol Evol 36:290-300; Altschul, S, F et al (1990) J Mol Biol 215:403-10. Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci.* USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci.* USA 90: 5873-5787. One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001. Alternatively, the UWGCG Package provides the BESTFIT program which can be used to calculate homology (for example used on its default settings) (Devereux et al (1984) *Nucleic Acids Research* 12, 387-395).

It will be understood that variants of polypeptides also includes substitution variants. Substitution variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| Ala | aliphatic, hydrophobic, neutral | Met | hydrophobic, neutral |
| --- | --- | --- | --- |
| Cys | polar, hydrophobic, neutral | Asn | polar, hydrophilic, neutral |
| Asp | polar, hydrophilic, charged (-) | Pro | hydrophobic, neutral |
| Glu | polar, hydrophilic, charged (-) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged (+) | Trp | aromatic, hydrophobic, neutral |
| Leu | aliphatic, hydrophobic, neutral | Tyr | aromatic, polar, hydrophobic |

The amino acid sequence of polypeptides for use in the invention may be modified to include non-naturally occurring chemistries or to increase the stability and targeting specificity of the compound. When the polypeptides are produced by synthetic means, such amino acids may be introduced during production. The polypeptides may also be modified following either synthetic or recombinant production.

A number of side chain modifications are known in the art and may be made to the side chains of the polypeptides, subject to the polypeptides retaining any further required activity or characteristic as may be specified herein.

Variant polypeptides as described in this section are those for which the amino acid sequence varies from that in SEQ ID NO: 1, but which retain the ability to be inserted into the membrane of an exosome.

The variant sequences typically differ by at least 1, 2, 3, 5, 10, 20, 30, 50, 100 or more mutations (which may be substitutions, deletions or insertions of amino acids). For example, from 1 to 100, 2 to 50, 3 to 30 or 5 to 20 amino acid substitutions, deletions or insertions may be made, provided the modified polypeptide is inserted into the membrane of an exosome.

Typically, polypeptides which are variants of Lamp-2 have more than about 50%, 55% or 65% identity, preferably at least 70%, at least 80%, at least 90% and particularly preferably at least 95%, at least 97% or at least 99% identity, with the amino acid sequence of SEQ ID NO: 1. The identity of variants of SEQ ID NO: 1 may be measured over a region of at least 30, 50, 100, 200, 250, 300, 350 or more contiguous amino acids of the sequence shown in SEQ ID NO: 1, or more preferably over the full length of SEQ ID NO: 1, excluding the signal sequence.

The fragment of the Lamp-2 polypeptide used in the targeting of exosomes of the invention is typically at least 55 amino acids, 100, 150, 200, or 250 amino acids in length.

The exosomal transmembrane protein is modified to incorporate a targeting moiety. Thus the exosomal transmembrane protein is expressed as a fusion protein comprising the targeting moiety. The targeting moiety is incorporated into the transmembrane protein such that it is positioned in the portion of the transmembrane protein present on the surface of the exosomes. In a preferred aspect of the present invention, the exosomal transmembrane protein is Lamp-2 and the targeting moiety is expressed as a fusion protein, wherein the targeting moiety is present near the N-terminus of Lamp-2 protein for example within 30, or within 20 amino acids of the Lamp-2 N terminal amino acid, not including the signal sequence.

Spacer or linker sequences may be provided between the targeting moiety and the remainder of the transmembrane protein for example to avoid interference from the targeting moiety in the folding of the transmembrane protein.

Linker or spacer sequences are typically 1 to 10 amino acids in length, typically 1 to 8 amino acids in length such as 2, 3 or 4 amino acids in length. Suitable amino acids for incorporation in linkers are alanine, arginine, serine or glycine. Suitable linkers include Ala-Arg and Ser-Gly-Gly.

In a particularly preferred aspect of the present invention, the transmembrane protein is Lamp-2 and the targeting moiety is present at or near the N-terminus of the protein, separated from Lamp-2 with linker sequences.

The targeting moiety may be introduced into the exosome by expressing the fusion protein comprising the targeting moiety and exosomal transmembrane protein within a cell used to produce the exosomes. Expression of this fusion protein in the cell, allows for the fusion protein to be incorporated into the exosome as it is produced from the cell.

For example, a polynucleotide construct such as a DNA plasmid, which expressed the fusion protein is transfected into the cell. Any suitable method can be used for introduction of the polynucleotide construct into the cell. The polynucleotide construct includes suitable promoter sequences so that the encoded fusion protein is expressed in the cell. Signal peptide sequences are also included so that the protein is incorporated into the membrane of the endoplasmic reticulum as it is produced. The membrane protein is then subsequently exported to the exosomal/lysosomal compartment before incorporation into the exosome. The signal sequence is typically a signal peptide sequence for an exosomal transmembrane protein. For example the signal peptide sequence is preferably derived from Lamp-2.

Preferred cells for production of exosomes are discussed in more detail above. Typically a preferred cell, such as an immature dendritic cells is transfected with a polynucleotide construct as described above, such that the fusion protein of the invention is expressed in the cell. Exosomes produced by the cell can then be collected. Such exosomes have the fusion protein inserted into the membrane such that the exosomes are targeted to the desired tissue or cell type through the targeting moiety.

Exosomes produced from cells can be collected from the culture medium by any suitable method. Typically a preparation of exosomes can be prepared from cell culture or tissue supernatant by centrifugation, filtration or combinations of these methods. For example, exosomes can be prepared by differential centrifugation, that is low speed (<20000 g) centrifugation to pellet larger particles followed by high speed (>100000 g) centrifugation to pellet exosomes, size filtration with appropriate filters (for example, 0.22 μm filter), gradient ultracentrifugation (for example, with sucrose gradient) or a combination of these methods.

In accordance with a preferred aspect of the present invention, the targeted exosomes are loaded with exogenous protein and/or peptide. In particular, in accordance with the present invention, exosomes are prepared with a targeting moiety as described herein and then loaded with the desired protein and/or for delivery or described above.

In other embodiments of the invention, a specific targeting moiety does not need to be included in the exosome. For example, exosomes may be administered directly to the site where therapy is required. Alternatively, direct targeting to a specific site may not be required and delivery, for example, intradermal or muscular delivery may be sufficient to generate the desired immune response without targeting exosomes to any specific cell type.

In some embodiments of the invention, no targeting moiety is included on the surface of the exosomes. However, the exosomes are selected such that they are more likely to target a specific tissue type. For example, exosomes derived from different cells may have natural affinities for specific cell subtypes as required by their physiological function such as the well-established affinity of mature dendritic cell-derived exosomes to T-cells. This affinity may be utilized to specifically deliver above-mentioned cargo to a tissue.

Delivery/Administration

The constructs of the invention may be administered by any suitable means. Administration to a human or animal subject may be selected from parenteral, intramuscular, intracerebral, intravascular (including intravenous), subcutaneous, intranasal, intracardiac, intracerebroventricular, intraperitoneal or transdermal administration. Typically the method of delivery is by injection. Preferably the injection is intramuscular or intravascular (e.g. intravenous). A physician will be able to determine the required route of administration for each particular patient.

The constructs are preferably delivered as a composition. The composition may be formulated for any suitable means of administration, including parenteral, intramuscular, intracerebral, intravascular (including intravenous), intracardiac, intracerebroventricular, intraperitoneal, subcutaneous, intranasal or transdermal administration. Compositions for parenteral administration may include sterile aqueous solutions which may also contain buffers, diluents and other suitable additives. The constructs of the invention may be formulated in a pharmaceutical composition, which may include pharmaceutically acceptable carriers, thickeners, diluents, buffers, preservatives, and other pharmaceutically acceptable carriers or excipients and the like in addition to the exosomes.

A "pharmaceutically acceptable carrier" (excipient) is a pharmaceutically acceptable solvent, suspending agent or any other pharmacologically inert vehicle for delivering one or more nucleic acids to a subject. Typical pharmaceutically acceptable carriers include, but are not limited to, binding agents (e.g. pregelatinised maize starch, polyvinylpyrrolidone or hydroxypropyl methylcellulose, etc); fillers (e.g. lactose and other sugars, microcrystalline cellulose, pectin, gelatin, calcium sulfate, ethyl cellulose, polyacrylates or calcium hydrogen phosphate, etc); lubricants (e.g. magnesium stearate, talc, silica, colloidal silicon dioxide, stearic acid, metallic stearates, hydrogenated vegetable oils, corn starch, polyethylene glycols, sodium benzoate, sodium acetate, etc); disintegrates (e.g. starch, sodium starch glycolate, etc); or wetting agents (e.g. sodium lauryl sulphate, etc).

The compositions provided herein may additionally contain other adjunct components conventionally found in pharmaceutical compositions. Thus, for example, the compositions may contain additional compatible pharmaceutically-active materials or may contain additional materials useful in physically formulating various dosage forms of the composition of present invention, such as dyes, flavouring agents, preservatives, antioxidants, opacifiers, thickening agents and stabilizers. However, such materials, when added, should not unduly interfere with the biological activities of the components of the compositions provided herein.

A therapeutically effective amount of composition is administered. The dose may be determined according to various parameters, especially according to the severity of the condition, age, and weight of the patient to be treated; the route of administration; and the required regimen. A physician will be able to determine the required route of administration and dosage for any particular patient. Optimum dosages may vary depending on the relative potency of individual constructs, and can generally be estimated based on EC50s found to be effective in vitro and in in vivo animal models. In general, dosage is from 0.01 mg/kg to 100 mg per kg of body weight. A typical daily dose is from about 0.1 to 50 mg per kg, preferably from about 0.1 mg/kg to 10 mg/kg of body weight, according to the potency of the specific construct, the age, weight and condition of the subject to be treated, the severity of the disease and the frequency and route of administration. Different dosages of the construct may be administered depending on whether administration is by intramuscular injection or systemic (intravenous or subcutaneous) injection. Preferably, the dose of a single intramuscular injection is in the range of about 5 to 20 μg. Preferably, the dose of single or multiple systemic injections is in the range of 10 to 100 mg/kg of body weight.

Due to construct clearance (and breakdown of any targeted molecule), the patient may have to be treated repeatedly, for example once or more daily, weekly, monthly or yearly. Persons of ordinary skill in the art can easily estimate repetition rates for dosing based on measured residence times and concentrations of the construct in bodily fluids or tissues. Following successful treatment, it may be desirable to have the patient undergo maintenance therapy, wherein the construct is administered in maintenance doses, ranging from 0.01 mg/kg to 100 mg per kg of body weight, once or more daily, to once every 20 years.

The invention is hereinafter described in more detail with reference to the following Examples.

EXAMPLES

Example 1

Loading of HEK Cells with HEK Exosomes Loaded with IgG Antibody

Figure 1:
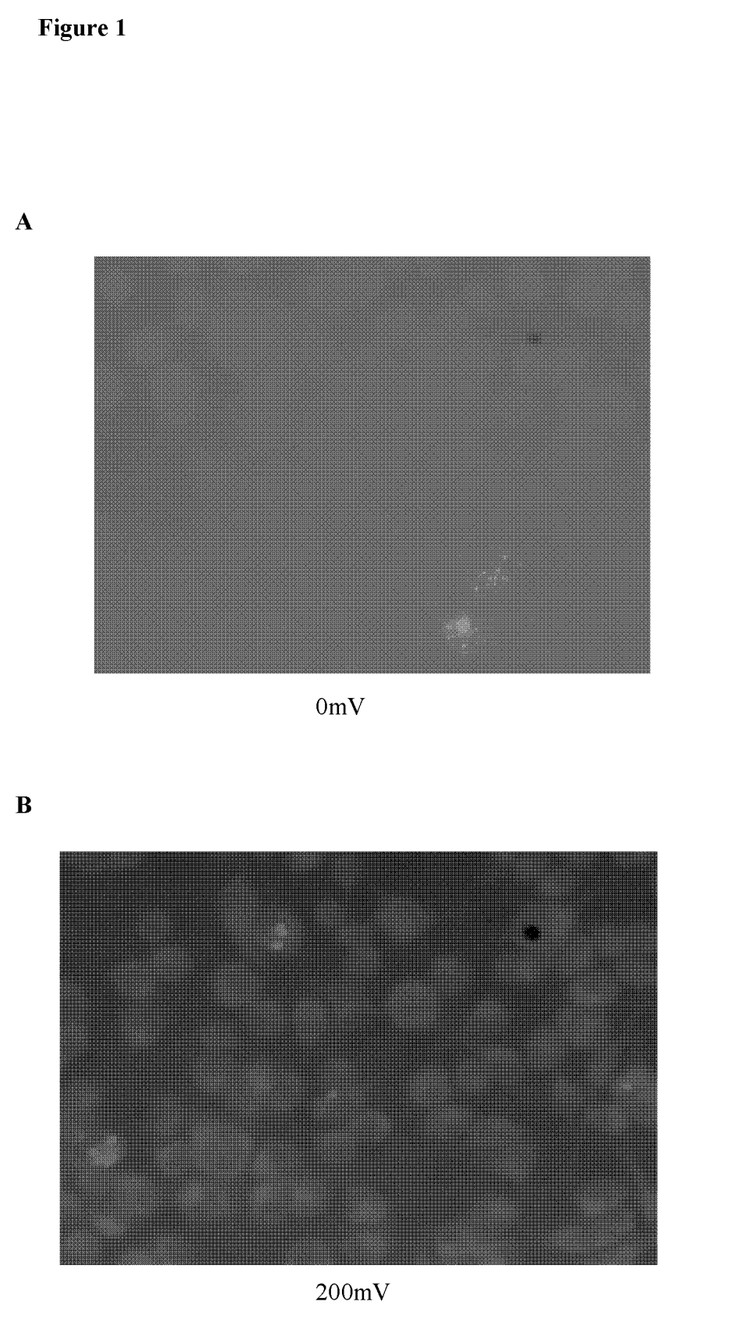
FIG. 1. Loading of HEK cells with HEK exosomes containing PE-conjugated IgG isotype antibody: A shows the localisation of the PE-conjugated antibody in HEK cells wherein the HEK exosomes were mixed, but not electroporated with, the antibody. B shows the localisation of the PE-conjugated antibody in HEK cells wherein the antibody was loaded into the HEK exosomes by electroporating at 200 mV.

Human embryonic kidney cell (HEK) exosomes were mixed with phycoerythrin (PE)-conjugated goat anti-rabbit IgG antibody in electroporation buffer (1.15 mM potassium phosphate pH 7.2, 25 mM KCl, 21% Optiprep) and either left unloaded (mixed with the antibody but not electroporated) or electroporated at 200 mV. The antibody-loaded exosomes were then added to HEK cells and incubated for two hours, by fluorescence measuring at 575 nm The HEK cells were then washed in phosphate-buffered saline (PBS) and imaged. FIG. 1 shows the cytoplasmic and nuclear localisation of the PE-antibody signal when cells were treated with exosomes loaded at 200 mV (B) as opposed to control exosomes which were mixed with the antibody but not electroporated (A).

Example 2

Loading of Human Fibroblasts with HEK Exosomes Loaded with FITC-Avidin

The transportan peptide GWTLNSAGYLLGKINLKA-LAALAKKIL (SEQ ID NO: 2) encoded by the polynucleotide sequence ggctggaccctgaacagcgcgggc-tatctgctgggcaaaattaacctgaaagcgctggcggcgctggcga aaaaaattctg (SEQ ID NO: 3) was inserted into the Lamp2b-expression vector previously described in International Publication No. WO/2010/119256.

The expression vector is based on pEGFP-C1 vector (Clonetech) from which the eGFP gene has been removed. Lamp2b was cloned with cDNA from C2C12 cells and XhoI and BspEI restriction sites were inserted after the signal peptide sequence together with glycine linkers (Ala-Arg-{Targeting Peptide}-Ser-Gly-Gly). The signal peptide of Lamp2b is required for membrane insertion but is cleaved off in the mature protein. The full construct was then cloned downstream of the CMV promoter with NheI and BamHI restriction sites into a pEGFP-C1 vector, removing the eGFP in the process.

The additional sequence added after the signal peptide containing the XhoI and BspEI sites enabled insertion of the transportan-coding sequence at the N-terminal part of Lamp2b.

The glycine linkers flanking the transportan targeting peptide prevent the transportan targeting peptide from influencing the folding of the Lamp2b protein. Ultimately, the transportan targeting peptide should be located on the external surface of the exosomes, hence conferring targeting capabilities to the exosomes.

The transportan targeting peptide of SEQ ID NO: 2 encoded by the polynucleotide sequence of SEQ ID NO: 3 was cloned into Lamp2b and transfected into dendritic cells 4 days before exosome purification. A major hindrance to the ability to express targeting ligands on the surface of exosomes is that primary dendritic cells are difficult to transfect and can potentially differentiate after transfection. Infection with viral vectors is not ideal either as dendritic cells are likely to be activated by the virus [30], hence producing immunostimulatory molecules that will be incorporated into the resultant exosomes. Minis Bio's TransIT-LT1 reagent was selected as it appeared to efficiently transduce dendritic cells without significantly activating dendritic cells. Transfection of HEK cells was performed with 5 µg of pLamp2b-transportan peptide expression vector and 5 µl of TransIT LT1 transfection reagent (Minis Bio) in a 6-well plate with 106 cells on day 4 after harvesting and isolation of exosomes is done on Day 8.

Figure 2:
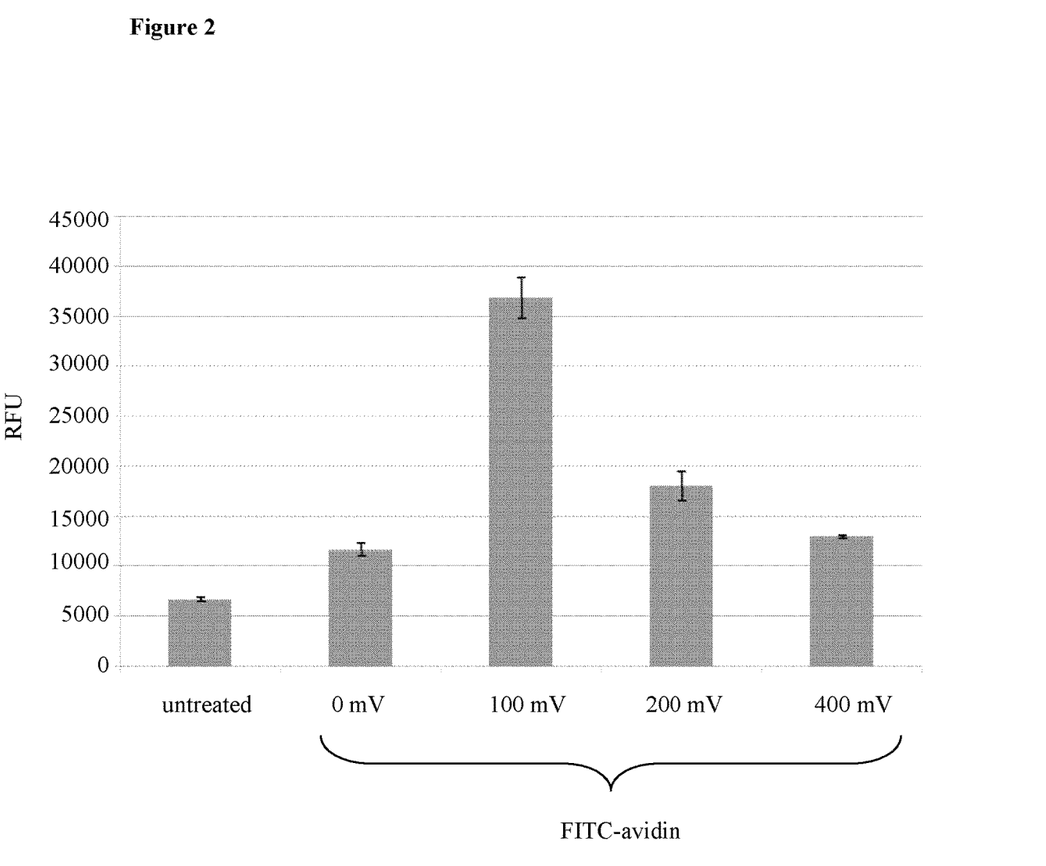
FIG. 2. Loading of human fibroblasts with HEK exosomes containing FITC-avidin: Transportan-Lamp2 exosomes were loaded with FITC-avidin by electroporation at 0 mV, 100 mV, 200 mV and 400 mV. The exosomes were then incubated with human fibroblasts and the amount of fluorescence emitted by the fibroblasts measured.

Transportan-Lamp2 exosomes (5 µg) derived from HEK cells were mixed with 5 µg FITC-avidin and electroporated at 0 mV, 100 mV, 200 mV and 400 mV. A control population of the exosomes was not treated with the FITC-avidin. Patient fibroblasts were treated for 3 h with the different exosome populations, after which the cells were washed three times with PBS and trypsinised to remove membrane-bound material. The fibroblast cells were then lysed and fluorescence measured at 490/520 nm. FIG. 2 shows that fibroblasts incubated with the untreated exosomes had the lowest level of fluorescence. Fibroblasts incubated with exosomes treated with FICT-avidin but and electroporated at 0 mV, 200 mV and 400 mV emitted more fluorescence than the cells treated with the control exosomes. However, cells incubated with exosomes treated with FITC-avidin and electroporated at 100 mV emitted the highest level of fluorescence, with an RFU of over 35,000.

[1] Raposo G, Nijman H W, Stoorvogel W, Liejendekker R, Harding C V, Melief D J Geuze H J (1996), B lymphocytes secrete antigen-presenting vesicles, *J Exp Med* 183:1161-1172.

[2] Zitvogel L, Regnault A, Lozier A, Wolfers J, Flament C, Tenza D, Ricciardi-Castagnoli P, Raposo G, Amigorena S (1998), Eradication of established murine tumors using a novel cell-free vaccine: dendritic cell-derived exosomes, *Nat Med* 4:594-600.

[3] Hao S, Moyana T, Xiang J (2007), Review: cancer immunotherapy by exosome-based vaccines, *Cancer Biother Radiopharm* 22:692-703.

[4] Valadi H, Ekström K, Bossios A, Sjöstrand M, Lee J J, Lötvall J O (2007), Exosome-mediated transfer of mRNAs and microRNAs is a novel mechanism of genetic exchange between cells, *Nat Cell Biol* 9(6):654-9.

[5] Skog J, Würdinger T, van Rijn S, Meijer D H, Gainche L, Sena-Esteves M, Curry W T Jr, Carter B S, Krichevsky A M, Breakefield X O (2008), Glioblastoma microvesicles transport RNA and proteins that promote tumour growth and provide diagnostic biomarkers, *Nat Cell Biol* 10(12): 1470-6.

[6] WO 2010/119256.

The invention claimed is:

1. A composition comprising a therapeutic delivery exosome and a pharmaceutically acceptable carrier, wherein the exosome is loaded with exogenous recombinant therapeutic monoclonal antibodies or antigen binding fragments thereof, and wherein the antibodies or antigen binding fragments thereof are encapsulated inside the exosome and do not elicit an immune response when inside the exosome.

2. A composition according to claim 1, wherein the exogenous recombinant therapeutic monoclonal antibodies or antigen binding fragments thereof are for use in a method of treatment of the human or animal body by therapy.

3. A composition according to claim 2, wherein the exogenous recombinant therapeutic monoclonal antibodies or antigen binding fragments thereof are for use in the treatment of cancer, autoimmune conditions, cardiovascular disease, haemophilia, sepsis, stroke, muscular dystrophy, muscular degeneration, Alzheimer's disease or organ or cell transplant rejection.

4. A composition according to claim 1, wherein said exosome comprises a targeting moiety expressed on the surface of the exosome.

5. A composition according to claim 4, wherein the targeting moiety comprises a peptide which binds to a moiety present on the cell to be targeted.

6. A composition according to claim 5, wherein the exosome comprises an exosomal transmembrane protein which has been modified to incorporate the peptide targeting moiety.

7. A composition according to claim 6, wherein the exosomal transmembrane protein is selected from Lamp-1, Lamp-2, CD13, CD86, Flotillin, or Syntaxin-3.

8. A composition according to claim 7, wherein the exosomal transmembrane protein is Lamp-2b.

* * * * *